US006855506B2

(12) United States Patent
Steiner et al.

(10) Patent No.: US 6,855,506 B2
(45) Date of Patent: Feb. 15, 2005

(54) FELINE PANCREATIC LIPASE COMPOSITION AND METHOD OF PREPARING AND USING SUCH COMPOSITION

(75) Inventors: Jörg M. Steiner, College Station, TX (US); David A. Williams, College Station, TX (US)

(73) Assignee: The Texas A&M University System, College Station, TX (US)

( * ) Notice: Subject to any disclaimer, the term of this patent is extended or adjusted under 35 U.S.C. 154(b) by 3 days.

(21) Appl. No.: 10/428,546

(22) Filed: May 2, 2003

(65) Prior Publication Data

US 2003/0207333 A1 Nov. 6, 2003

Related U.S. Application Data

(60) Provisional application No. 60/377,522, filed on May 3, 2002.

(51) Int. Cl.[7] ............................................. G01N 33/567
(52) U.S. Cl. .......................... 435/7.2; 435/7.1; 435/7.2; 435/7.92; 435/68.1; 435/69.7; 435/183; 435/198
(58) Field of Search ............................. 435/198, 7.1, 4, 435/7.92, 68.1, 69.7, 183, 7.2

(56) References Cited

PUBLICATIONS

Steiner et al., Feline Pancreatitis, Compendium on Continuing Education for the Practicing Veterinarian, (May 1997) vol. 19, No. 5, pp. 590–602.*
Steiner et al., Feline Exocrine Pancreatic Disorders, Veterinary Clinics of North America: Small Animal Practice, vol. 29, No. 2, Mar. 1999, p. 571–575.*
Simpson et al, Ante mortem diagnosis in four cats, Journal of Small Animal Practice (1994), vol. 35, pp. 93–99).*

Hofmann–Lehmann et al. Parameters of Disease Progression in Long–Term Experimental Feline Retrovirus (Feline Immunodeficiency Virus and Feline Leukemia Virus) Infections: Hematology, clinical chemistry, and lymphocyte subsets. Clinical and Diagnostic.
Laboratory Immunology, Jan. 1997, vol. 4, No. 1, pp. 33–42
Crenon et al. Pancreatic lipase–related protein type I: a specialized lipase or an inactive enzyme. Protein Engineering, 1998, vol. 11, No. 2, pp. 135–142.
Ginzinger et al. A Mutation in the Lipoprotein Lipase Genes is the Molecular Basis of Chylomicronemia in a Colony of Domestic Cats. J. Clinical. Investigation, 1996, vol. 97, pp. 1257–1266.
Denham et al. Cationic Liposome–Mediated Gene Transfer During Acute Pancreatitis: Tissue Specificity, Duration, and Effects of Acute Inflammation. J. Gastroint. Surg., 1998, vol. 2, pp. 95–101.

(List continued on next page.)

Primary Examiner—James Housel
Assistant Examiner—Deborah A Davis
(74) Attorney, Agent, or Firm—Bracewell & Patterson LLP (57) ABSTRACT

A novel form of lipase, namely feline pancreatic lipase (also termed feline classical pancreatic lipase) has an N-terminal amino acid sequence as shown in SEQ ID NO. 1. A method of purifying this lipase includes collecting pancreatic tissue from cats, delipidating the pancreatic tissue to produce a delipidated pancreatic extract, extracting pancreatic lipase from the delipidated pancreatic extract, and eluting the extracted pancreatic lipase through various columns. This lipase can be used for measuring pancreatic lipase immunoreactivity in serum thereby diagnosing pancreatitis in cats. To do so, antiserum against feline pancreatic lipase is prepared, and immunoassays are then performed in serum samples using this antiserum. In the event that increased concentration of pancreatic lipase immunoreactivity above the control range is detected in the serum, the cat might have pancreatitis.

8 Claims, 5 Drawing Sheets

OTHER PUBLICATIONS

Anderson,R.A., Sando,G.N., 1991. Cloning and expression of cDNA encoding human lysosomal acid lipase/cholesteryl ester hydrolase. Similarities to gastric and lingual lipases. J. Biol. Chem. 266, 22479–22484.

Antonian,E., 1988. Recent advances in the purification, characterization and structure determination of lipases. Lipids 23, 1101–1106.

Bianchetta,J.D., Bidaud,J., Guidoni,A.A., Bonicel,J.J., Rovery,M., 1979. Porcine pancreatic lipase. Sequence of the first 234 amino acids of the peptide chain. Eur. J. Biochem. 97, 395–405.

Bosc–Bierne,I., Rathelot,J., Perrot,C., Sarda,L., 1984. Studies on chicken pancreatic lipase and colipase. Biochim. Biophys. Acta 794, 65–71.

Bousset–Risso,M., Bonicel,J., Rovery,M., 1985. Limited proteolysis of porcine pancreatic lipase. Lability of the Phe 335–Ala 336 bond towards chymotrypsin. Febs Lett. 182, 323–326.

Carrière,F., Barrowman,J.A., Verger, R., Laugier,R., 1993a. Secretion and contribution to lipolysis of gastric and pancreatic lipases during a test meal in humans. Gastroenterol. 105, 876–888.

Carrière,F., Bezzine,S., Verger,R., 1997. Molecular evolution of the pancreatic lipase and two related enzymes towards different substrate selectivities. Journal of Molecular Catalysis B: Enzymatic 3, 55–64.

Carrière,F., Gargouri, Y., Moreau,H., Ransac,S., Rogalska, E., Verger,R., 1994. Gastric lipases: cellular, biochemical and kinetic aspects. In: Woolley,P., Peterson,S.B. (Eds.), Lipases—their structure, biochemistry, and application, Cambridge University Press, Cambridge, pp. 181–205.

Carrière,F., Laugier,R., Barrowman,J.A., Douchet,I., Priymenko,N., Verger,R., 1993b. Gastric and pancreatic lipase levels during a test meal in dogs. Scand. J. Gastroenterol. 28, 443–454.

Carrière,F., Moreau,H., Raphel,V., Laugier,R., Benicourt,C., Junien,J.–L., Verger,R., 1991. Purification and biochemical characterization of dog gastric lipase. Eur. J. Biochem. 202, 75–83.

Carrière,F., Withers–Martinez,C., Van Tilbeurgh,H., Roussel,A., Cambillau,C., Verger,R., 1998. Structural basis of the substrate selectivity of pancreatic lipases and some related proteins. Biochim. Biophys. Acta Rev. Biomembr. 1376, 417–432.

De Caro,A., Bonicel,J., Pieroni,G., Guy,O., 1981. Comparative studies of human and porcine pancreatic lipases: N–terminal sequences, sulfhydryl groups and interfacial activity. Biochimie 63, 799–801.

De Caro,J., Carrière,F., Barboni,P., Giller,T., Verger,R., De Caro,A., 1998. Pancreatic lipase–related protein 1 (PLRP1) is present in the pancreatic juice of several species. Biochim. Biophys. Acta 1387, 331–341.

Freed,L.M., York,C.M., Hamosh,P., Mehta,N.R., Hamosh, M., 1987. Bile salt–stimulated lipase of human milk: characteristics of the enzyme in the milk of mothers of premature and full–term infants. J Pediatr. Gastroenterol Nutr. 6, 598–604.

Gieseg,S.P., Forrester,I.T., Carne,A., 1992. The purification of ovine pancreatic lipase that is free of colipase using an improved delipidation method. Pancreas 7, 45–51.

Hirata,K., Dichek,H.L., Cioffi,J.A., Choi,S.Y., Leeper,N.J., Quintana,L., Kronmal,G.S., Cooper,A.D., Quertermous,T., 1999. Cloning of a unique lipase from endothelial cells extends the lipase gene family. J. Biol. Chem. 274, 14170–14175.

Jaeger,K.E., Ransac,S., Dijkstra,B.W., Colson,C., van Heuvel,M., Misset,O., 1994. Bacterial lipases. FEMS Microbiology Reviews 15, 29–63.

Kerfelec,B., Foglizzo,E., Bonicel,J., Bougis,P.E., Chapus, C., 1992. Sequence of horse pancreatic lipase as determined by protein and cDNA sequencing—Implications for p–nitrophenyl acetate hydrolysis by pancreatic lipases. Eur. J. Biochem. 206, 279–287.

Lawson,D.M., Brzozowski,A.M., Dodson,G.G., Hubbard, R.E., Huge–Jensen,B., Boel,E., Derewenda,Z.S., 1994. Three–dimensional structures of two lipases from filamentous fungi. In: Woolley,P., Petersen,S.B. (Eds.), Lipases—their structure, biochemistry and application, Cambridge University Press, Cambridge, pp. 77–94.

Leger,C., Charles,M., 1980. Pancreatic lipase. World Review of Nutrition & Dietetics 35, 96–128.

Lin,Y.H., Yu,C., Huang,A.H., 1986. Substrate specificities of lipases from corn and other seeds. Arch. Biochem. Biophys. 244, 346–356.

Mejdoub,H., Reinbolt,J., Gargouri,Y., 1994. Dromedary pancreatic lipase: Purification and structural properties. Biochem. Biophys. Acta. Lipids Lipid Metab. 1213, 119–126.

Moreau,H., Gargouri,Y., Lecat,D., Junien,J.L., Verger,R., 1988. Screening of preduodenal lipases in several mammals. Biochim. Biophys. Acta 959, 247–252.

Mukherjee,K.D., Hills,M.J., 1994. Lipases from plants. In: Woolley,P., Petersen,S.B. (Eds.), Lipases—their structure, biochemistry and application, Cambridge University Press, Cambridge, pp. 49–75.

Petersen,S.B., Drabløs,F., 1994. A sequence analysis of lipases, esterases, and related proteins. In: Woolley,P., Petersen,S.B. (Eds.), Lipases—their structure, biochemistry, and application, Cambridge University Press, Cambridge, pp. 23–48.

Rathelot,J., Julien,R., Bosc–Bierne,I., Gargouri,Y., Canioni, P., Sarda,L., 1981. Horse pancreatic lipase. Interaction with colipase from various species. Biochimie 63, 227–234.

Smith,P.K., Krohn,R.I., Hermanson,G.T., Mallia,A.K., Gartner,F.H., Provenzano,M.D., Fujimoto,E.K., Goeke,N.M., Olson,B.J., Klenk,D.C., 1985. Measurement of protein using bicinchoninic acid. Anal. Biochem. 150, 76–85.

Steiner,J.M., Williams,D.A., 2002. Purification of classical pancreatic lipase from dog pancreas. Biochimie 84 (2002) 1243–1251.

Steiner,J.M., Berridge,B.R., Wojcieszyn,J., Williams,D.A., 2002. Cellular immunolocalization of gastric and pancreatic lipase in various tissues obtained from dogs. Am. J. Vet. Res. 63, 722–727.

Steiner, J.M., Broussard, J., Mansfield, C.S., Gumminger, S.R., Williams, D.A. 2001a. Serum canine pancreatic lipase immunoreactivity (cPLI) concentrations in dogs with spontaneous pancreatitis. J. Vet. Int. Med. 15, 274.

Steiner, J.M., Gumminger, S.R., Rutz, G.M., Williams, D.A. 2000b. Serum canine pancreatic lipase immunoreactivity (cPLI) concentrations in dogs with exocrine pancreatic insufficiency. J. Vet. Int. Med. 15, 274.

Steiner, J.M., Gumminger, S.R., Williams, D.A. 2000 c. Development and validation of an enzyme–linked immunosorbent assay (ELISA) for the measurement of canine pancreatic lipase immunoreactivity (cPLI) in serum. J. Vet. Int. Med. 15, 311.

Svendsen,A., 1994. Sequence comparisons within the lipase family. In: Woolley,P., Petersen,S.B. (Eds.), Lipases—their structure, biochemistry, and application, Cambridge University Press, Camridge, pp. 1–21.

Vandermeers,A., Chroistophe,J., 1968. Alpha–amylase and lipase of rat pancreas. Chromatographic purification and research on molecular weight and amino acid composition. Biochim. Biophys. Acta 154, 110–129.

Verger,R., Haas,G.H., Sarda,L., Desnuelle, 1969. Purification from porcine pancreas of two molecular species with lipase activity. Biochim. Biophys. Acta 188, 272–282.

Winkler,F.K., D'Arcy,A., Hunziker,W., 1990. Structure of human pancreatic lipase. Nature 343, 771–774.

* cited by examiner

```
        1   2   3   4   5   6   7   8   9   10  11  12  13  14  15  16  17  18  19  20  21  22  23  24  25
ePL    Lys-Glu-Ile- ? -Phe-Pro-Arg-Leu-Gly- ? -Phe-Ser-Asp-Asp-Ala-Pro-Trp-Ala-Gly-Ile-Val-Gln-Arg-Pro-Leu
(SEQ ID NO. 1)

pPL    Ser-Glu-Val-Cys-Phe-Pro-Arg-Leu-Gly-Cys-Phe-Ser-Asp-Asp-Ala-Pro-Trp-Ala-Gly-Ile-Val-Gln-Arg-Pro-Leu
(SEQ ID NO. 2)

cPL    Lys-Glu-Val-Cys-Phe-Pro-Arg-Leu-Gly-Cys-Phe-Ser-Asp-Asp-Ser-Pro-Trp-Ala-Gly-Ile-Val-Glu-Arg-Pro-Leu
(SEQ ID NO. 3)

cPLRP1 Lys-Glu-Val-Cys-Tyr-Glu-Gln-Ile-Gly-Cys-Phe-Ser-Asp-Ala-Glu-Pro-Trp-Ala-Gly-Thr-Ala-Ile-Arg-Pro-Leu
(SEQ ID NO. 4)

ePL    Asn-Glu-Val-Cys-Tyr-Glu-Arg-Leu-Gly-Cys-Phe-Ser-Asp-Asp-Ser-Pro-Trp-Ala-Gly-Ile-Val-Glu-Arg-Pro-Leu
(SEQ ID NO. 5)

hPL    Lys-Glu-Val-Cys-Tyr-Glu-Arg-Leu-Gly-Cys-Phe-Ser-Asp-Asp-Ser-Pro-Trp-Ser-Gly-Ile-Thr-Glu-Arg-Pro-Leu
(SEQ ID NO. 6)
```

Figure 5

FELINE PANCREATIC LIPASE COMPOSITION AND METHOD OF PREPARING AND USING SUCH COMPOSITION

CROSS-REFERENCE TO RELATED APPLICATIONS

This nonprovisional application claims priority of U.S. Provisional patent application Ser. No. 60/377,522, filed on May 3, 2002.

BACKGROUND OF THE INVENTION

1. Field of the Invention

The present invention relates generally to the field of biology and medicine. More particularly, the present invention relates to feline pancreatic lipase compositions, methods for preparing such compositions, and methods for employing such compositions to detect the concentration of pancreatic lipase in cat serum for diagnosis and management of pancreatitis.

2. Description of Related Art

Lipases are water-soluble enzymes that hydrolyze water-insoluble substrates into more polar lipolysis products (Petersen and Drabløs, 1994). In 1856 Claude Bernard identified the first lipase (Petersen and Drabløs, 1994). Since then a plethora of lipases has been identified in microorganisms, plants, and animals (Lin et al., 1986; Jaeger et al., 1994; Petersen and Drabløs, 1994; Mukherjee and Hills, 1994; Lawson et al., 1994). Lipases share a common triad of amino acids (serine, aspartic or glutamic acid, and histidine) in the active site, which is also shared with serine proteases (Svendsen, 1994). Another common feature of almost all lipases are glycosylation site motifs (Antonian, 1988). Many lipases have been shown to be related phylogenetically. The pancreatic lipase gene family is a large gene family with 9 subfamilies (Petersen and Drabløs, 1994; Carrière et al., 1997; Carrière et al., 1998; Hirata et al., 1999). In addition there are other groups of phylogenetically related lipases, and yet other lipases that do not belong to a defined gene family (Anderson and Sando, 1991).

The main function of lipases is the hydrolysis of lipids. A lipase is needed whenever an apolar lipid needs to cross a biological membrane. Triglycerides are prime examples of apolar lipids. Thus lipase is needed in order for triglycerides to be absorbed from the intestinal tract. There are two digestive lipases in most vertebrate species, i.e., a preduodenal lipase and classical pancreatic lipase (Carrière et al., 1994). In addition, in neonates, lipase for digestion of triglycerides is also supplied through milk (Freed et al., 1986; Freed et al., 1987). This lipase is known as bile salt-stimulated lipase (Freed et al., 1986; Freed et al., 1987). Even though it is crucial for the digestion of triglycerides in milk, bile salt-stimulated lipase is not considered as a digestive lipase, as it is not utilized as a digestive lipase in the organism where it was synthesized. Preduodenal lipase has been shown to originate from a single tissue in all species examined to date (Moreau et al., 1988). A pharyngeal lipase was identified in cows and sheep, a lingual lipase in rats and mice, and a gastric lipase in human beings, monkeys, horses, pigs, guinea pigs, cats, and dogs (Moreau et al., 1988). No preduodenal lipase could be identified in chickens (Moreau et al., 1988). In human beings and dogs it has been shown that gastric lipase contributes significantly to the digestion of dietary triglycerides (Carrière et al., 1993a; Carrière et al., 1993b). However, pancreatic lipase (also called classical pancreatic lipase) is the most important enzyme in the digestion of dietary triglycerides (Carrière et al., 1991; Carrière et al., 1993a).

It has recently been shown by immunolocalization that pancreatic lipase is only present in pancreatic acinar cells in clinically healthy dogs, suggesting that classical pancreatic lipase may be an ideal marker for function and pathology of the exocrine pancreas (Steiner et al., 2002). This hypothesis has been confirmed in clinical studies that have shown that the measurement of pancreatic lipase immunoreactivity in serum is a specific marker for exocrine pancreatic function and also highly sensitive for pancreatitis in the dog (Steiner et al., 2001a; Steiner et al., 2001b; Steiner et al., 2001c). The purification of classical pancreatic lipase has been reported in many species (Vandermeers and Chroistophe, 1968; Rathelot et al., 1981; Bosc-Bieme et al., 1984; Gieseg et al., 1992; Mejdoub et al., 1994; Steiner and Williams, 2003). However, the purification of feline classical pancreatic lipase has not been reported previously.

Pancreatitis is a common gastrointestinal disorder in cats and is characterized by the autodigestion of the exocrine pancreas. Clinical symptoms of feline pancreatitis are non-specific and the disease can be difficult to diagnose. Pancreatitis is associated with an increased amount of digestive enzymes and zymogens leaking into the blood stream. One of these enzymes is pancreatic lipase. A number of assays have been developed to detect the presence of lipase in serum by use of catalytic assays. However, these assays lack both sensitivity and specificity for pancreatitis in both human beings and dogs. Furthermore, these assays for the quantification of lipase activity have been shown to have no clinical utility in the diagnosis of feline pancreatitis.

Therefore, there is a long-standing need for an effective method to prepare and purify feline pancreatic lipase as well as an effective method to diagnose feline pancreatitis.

SUMMARY OF THE INVENTION

The present invention provides a novel lipase, namely feline pancreatic lipase (fPL; also termed feline classical pancreatic lipase). This lipase has an N-terminal amino acid sequence as shown in SEQ ID NO. 1 and has been shown to have a molecular mass of approximately 52.5 kDa on sodium dodecyl sulfate polyacrylamide gel electrophoresis (SDS-PAGE) and exact molecular mass of 52.4 kDa by mass spectrometry. N-terminal amino acid sequence of the first 25 amino acid residues of this lipase has shown to have close homology with the amino acid sequence of classical pancreatic lipase in other species.

The present invention also provides a method of purifying feline classical pancreatic lipase from pancreatic tissue. This method preferably includes collecting pancreatic tissue from cats, delipidating the pancreatic tissue to produce a delipidated pancreatic extract, extracting pancreatic lipase from the delipidated pancreatic extract, and eluting the extracted pancreatic lipase through various columns.

The present invention further provides a method of employing this new form of lipase. This method preferably comprises radioimmunoassays and other immunoassays (e.g. ELISA) for the measurement of lipase immunoreactivity in serum thereby providing a clinically useful diagnostic tool for pancreatitis in cats. Specifically, this method advantageously includes preparing antiserum against feline pancreatic lipase, and performing immunoassays in serum samples using this antiserum or a preparation thereof. By doing so, feline pancreatic lipase immunoreactivity is measured in serum. In the event that increased concentration of pancreatic lipase immunoreactivity above a control range is detected in the serum, the cat might have pancreatitis.

The foregoing and other advantages of the present invention will be apparent to those skilled in the art, in view of the following detailed description of the preferred embodiment of the present invention, taken in conjunction with the accompanying drawings.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

The present invention discloses a novel pancreatic lipase in cats and a method of purifying such lipase from pancreatic tissue in cats. This protein has been partially characterized and shown to have a molecular mass of approximately 52.5 kDa by sodium dodecyl sulfate polyacrylamide gel electrophoresis, and an exact molecular mass of 52.4 kDa by mass spectrometry. The N-terminal amino acid sequence of this lipase has been obtained (see SEQ ID NO. 1) and the amino acid sequence of the first 25 amino acid residues shows to have close homology with the amino acid sequence of classical pancreatic lipase in other species.

For purification, pancreatic tissue was collected from cats (*Felis catus*) sacrificed for unrelated research projects. Fat was removed by trimming away grossly visible fat and by extraction in organic solvents. The delipidated pancreatic extract was further purified by extracting the enzymes in a Tris-buffer containing two different protease inhibitors, benzamidine and phenylmethylsulfonyl fluoride, followed by anion-exchange, size-exclusion, and cation-exchange chromatography.

The present invention also provides methods of employing the novel feline pancreatic lipase for diagnosis and management of pancreatitis in cats.

The present invention is directed to a novel lipase, namely feline pancreatic lipase (fPL; also termed feline classical pancreatic lipase), having an N-terminal amino acid sequence as shown in SEQ ID NO. 1

The present invention is also directed to a method of purifying feline classical pancreatic lipase from pancreatic tissue. This method preferably includes collecting pancreatic tissue from cats, delipidating the pancreatic tissue to produce a delipidated pancreatic extract, extracting pancreatic lipase from the delipidated pancreatic extract, and eluting the extracted pancreatic lipase through various columns.

Preferably, the step of delipidation further includes removing gross fat from the pancreatic tissue using a sharp object; homogenizing the remaining pancreatic tissue in organic solvents; and filtering the homogenized pancreatic tissue to obtain a delipidated pancreatic extract. Representative examples of the organic solvents include acetone, a mix of chloroform and 1-butanol, and ethyl ether.

Still preferably, the step of extraction further includes suspending the delipidated pancreatic extract in a Tris-buffer containing protease inhibitor(s); and centrifuging the suspension to obtain the supernatant which contains the pancreatic lipase. Representative examples of protease inhibitor (s) include benzamidine and phenylmethylsulfonyl fluoride.

Still preferably, the columns for eluting the extracted pancreatic lipase include anion-exchange chromatography columns, size-exclusion chromatography columns, and cation-exchange chromatography columns.

The present invention is further directed to a method of measuring feline pancreatic lipase immunoreactivity in serum thereby diagnosing pancreatitis in cats. This method advantageously includes preparing antiserum against feline pancreatic lipase, and performing immunoassays in serum samples using the antiserum. By doing so, feline pancreatic lipase immunoreactivity is measured in serum. In the event that increased concentration of pancreatic lipase immunoreactivity above a control range is detected in the serum, the cat might have pancreatitis.

Preferably, feline pancreatic lipase has an N-terminal amino acid sequence as shown in SEQ ID NO. 1, and is labeled for evaluation of the prepared antiserum. An example of the label is $^{125}I$, and the immunoassay used is a radioimmunoassay. Still preferably, the control range for feline pancreatic lipase immunoreactivity in cat serum is established from a pool of clinically healthy cats using the central 95th percentile and is preferably from about 2.0 µg/L to about 6.7 µg/L.

The following examples are given for the purpose of illustrating various embodiments of the invention and are not meant to limit the present invention in any fashion.

EXAMPLE 1
Purification of Feline Pancreatic Lipase (fPL) from Pancreatic Tissue Pancreata were collected from cats sacrificed for unrelated research projects and stored frozen at −20° C. until further use. All standard laboratory equipment including the Buchner funnel was purchased from VWR Scientific, West Chester, Pa. All columns, chromatographic gels, pumps, fraction collector and UV-monitor were purchased from Amersham Biosciences, Uppsala, Sweden. The pH stat titration system (Metrohm 718 STAT Titrino) and the tissue grinder (Polytron PT-MR 2100) were purchased from Brinkmann Instruments, Westbury, N.Y. Supplies for electrophoresis were purchased from Invitrogen, Carlsbad, Calif., USA. All chemical agents were purchased from Sigma Chemicals, St. Louis, Mo., USA. The BCA protein assay kit was acquired from Pierce Chemical Company, Rockford, Ill., USA. Disposable size-exclusion chromatography columns and concentrators (Ultrafree centrifugal filter device; 10K) were purchased from Bio Rad, Hercules, Calif., USA and Waters Corporation, Milford, Mass., USA, respectively.

For purification, frozen pancreatic tissue was thawed at room temperature and gross fat removed with a scalpel blade. Pancreatic tissue was then cut into small pieces, homogenized with a tissue grinder, and delipidated using organic solvents. First, feline pancreas was homogenized in acetone. The material was filtered through a medium Buchner funnel (pore size 10–15 $\mu$m) using vacuum suction. The filtrate was again homogenized with the tissue grinder in acetone and filtered through the medium Buchner funnel. This procedure was repeated one more time. The filtrate was then homogenized in a mixture of 9 to 1 of chloroform and 1-butanol and filtered through the medium Buchner funnel. This procedure was repeated two more times, followed by the same procedure using a mixture of 4 to 1 of chloroform and 1-butanol two more times. Finally, the filtrate was carefully dissolved in ethyl ether and filtered to dryness through the medium Buchner funnel. The filtrate was broken up into a fine powder by carefully stirring with a metal spatula and the delipidated pancreatic extract was kept at −20° C. until further purification.

Protein was extracted from delipidated pancreas powder by suspending approximately 2 g of the powder in 25 ml of 20 mM Tris-HCl, 2 mM benzamidine, 150 mM NaCl, pH 7.5 and adding 250 $\mu$l 100 mM phenylmethylsulfonyl fluoride (PMSF) in isopropyl alcohol. Benzamidine and PMSF served as protease inhibitors. The suspension was thoroughly mixed for 1 min using a tissue grinder and was further mixed for 20 min at 4° C. using a rocking plate. This was followed by centrifugation for 15 min at approximately 10,000 g and 4° C. The supernatant was evaluated for absorbance at 280 nm and for lipolytic activity, and was saved. A disposable gel-filtration column was used to change the buffer of the pooled supernatant to 10 mM Tris-HCl, 2 mM benzamidine, 1 mM PMSF, pH 8.0 (buffer A) at 4° C. following manufacturer's instructions.

Feline pancreatic lipase was further purified by anion exchange chromatography on a pre-packed Mono Q® column. The pancreatic lipase solution was applied to the column in buffer A and the column was washed until the absorbance monitor at a wavelength of 280 nm had returned to the base line. Feline pancreatic lipase was eluted using a continuous NaCl gradient from 0 to 80 mM NaCl over 30 min in buffer A at a flow rate of 1 ml/min. Lipase activity-containing fractions were pooled, concentrated, the buffer changed to 10 mM MES, 2 mM benzamidine, 1 mM PMSF, pH 6.0 using a concentrating device with a 10,000 MW pore size, and saved for further purification.

Further purification of fPL was achieved by size-exclusion chromatography on a Sephacryl S-300 HR® column using a mobile phase of 10 mM MES, 2 mM benzamidine, 1 mM PMSF, pH 6.0 at a flow rate of 1 ml/min. Fractions containing lipase activity were pooled, concentrated, and the buffer changed to 10 mM MES, pH 6.0 using a concentrating device with a 10,000 MW pore size.

Final purification of feline pancreatic lipase was achieved by cation exchange chromatography on a self-packed Source S® column. The pancreatic lipase mixture was applied in 10 mM MES, pH 6.0 at a flow rate of 1 ml/min. After return of the absorbance monitor at 280 m to the base line, a linear NaCl gradient from 0 to 200 mM over 120 min was applied at a flow rate of 1 ml/min. The fraction with the highest specific lipase activity was collected, concentrated, and the buffer changed to phosphate buffered saline (100 mM sodium phosphate, 150 mM NaCl, pH 7.2) using a concentrating device with a 10,000 MW pore size. The concentration of the purified fPL was adjusted to an absorbance of $A_{280}=0.55$, aliquotted, and frozen at −80° C.

EXAMPLE 2
Lipolytic Activity Measurement during the Purification of Feline Pancreatic Lipase (fPL)

Lipolytic activity during purification was measured by a pH stat method using tributyrin as a substrate in the presence of colipase. For this purpose an acidic colipase preparation of feline colipase had been previously prepared. Briefly, 1 g of delipidated feline pancreatic extract was suspended in 50 ml 20 mM Tris-HCl, 3.3 mM $CaCl_2$, 2 mM benzamidine, 5 mM 3-phenyl propionate, 1 mM PMSF (added in isopropyl alcohol), pH 8.0 and mixed at 4° C. for 2 hr. The mixture was centrifuged at approximately 12,000 g and 4° C. for 30 min and the precipitate was discarded. Lipase activity was measured and the pH adjusted to pH 2.0 using 6 N HCl. The solution was once again centrifuged under above conditions and the supernatant was saved. After measuring lipase activity the solution was adjusted to pH 5.0 using 2 N NaOH. After further centrifugation under above conditions aliquots of the supernatant were frozen at −20° C. For detection of lipase activity a volume of 0.5 ml tributyrin was added to 14.5 ml of 0.28 mM Tris-HCl, 1.4 mM $CaCl_2$, 4.0 mM taurodeoxycholate, 150 mM NaCl, pH 8.0 in a reaction vessel kept at 37° C. 50 microliters of the acidic feline colipase preparation estimated to result in at least a 2 to 1 molar excess of feline colipase to feline pancreatic lipase were added to the mixture and the pH readjusted to 8.0. 10 microliters of the sample were added to the reaction vessel and the pH was kept at 8.0 by controlled addition of 100 mM NaOH. After a waiting period of 1 min use of NaOH solution to maintain constant pH at 8.0 was measured for 3 minutes and lipolytic activity was expressed in international units, 1 unit being the amount of lipolytic activity releasing 1 $\mu$mol of titratable fatty acid per minute under described conditions.

EXAMPLE 3
Characterization of Purified Feline Pancreatic Lipase (fPL)

The molecular mass of purified feline pancreatic lipase was estimated by SDS-PAGE following manufacturer's instructions. The gel was stained with a Coomassie blue type stain. A more exact determination of the molecular mass was achieved using mass spectrometry performed by the Mass Spectrometry Laboratory, Department of Chemistry, Texas A&M University, College Station, Tex.

Specific absorbance of fPL was determined by measurement of the protein concentration of a serial dilution of feline pancreatic lipase in PBS, pH 7.2 with a known absorbance at a wavelength of 280 nm using a BCA protein assay (Smith et al., 1985).

N-terminal amino acid sequence for the first 25 amino acid residues was determined by Edman degradation using an automated amino acid sequence analyzer at the Department of Biochemistry, Purdue University, West-Lafayette, Ind.

EXAMPLE 4
Characteristics of Feline Pancreatic Lipase (fPL)

Figure 1:
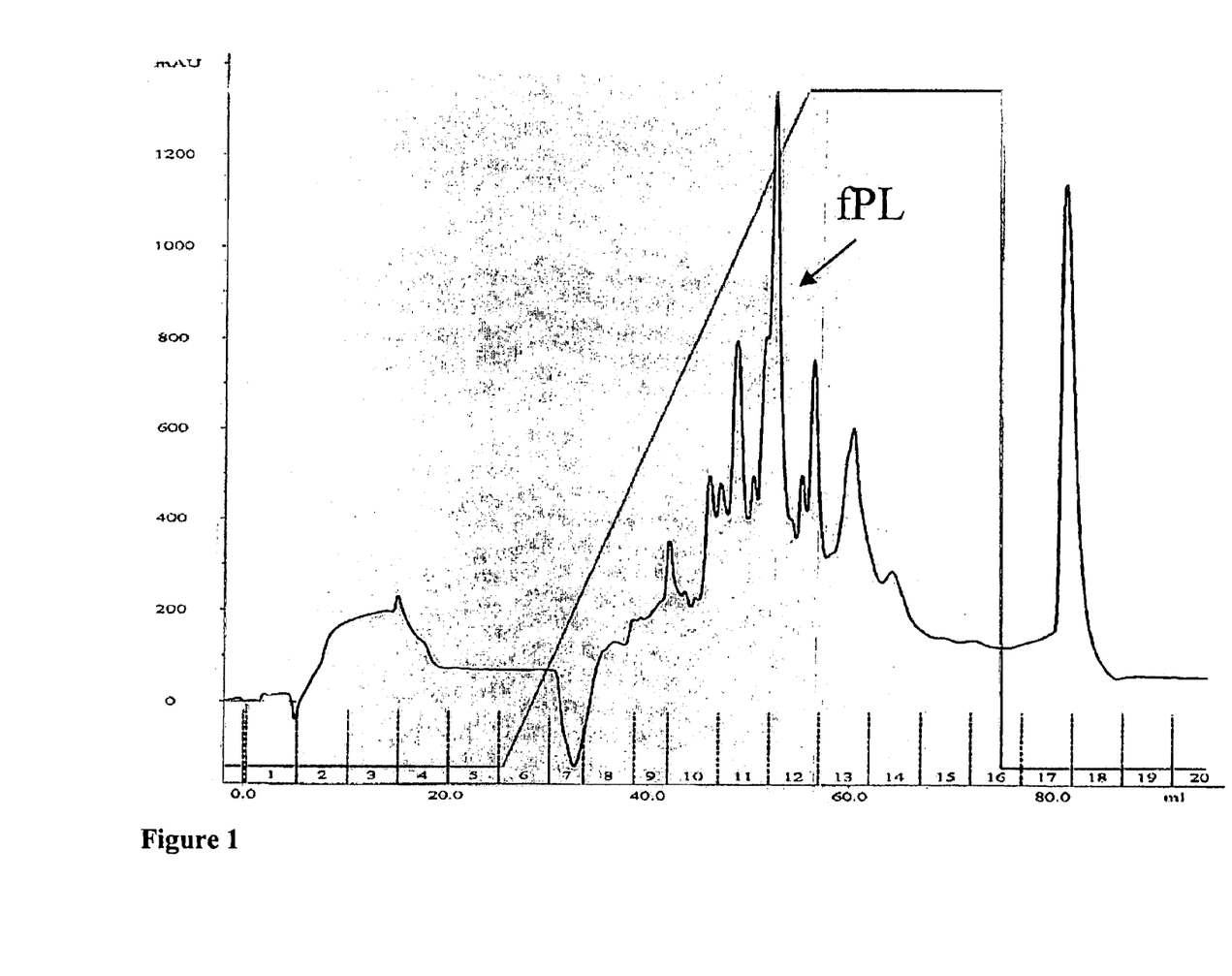
FIG. 1 shows anion-exchange chromatography of aqueous feline pancreatic extract after buffer change using a PD-10 column. The darker line shows the absorbance at a wavelength of 280 nm during chromatography. The lighter line shows the concentration of NaCl. The dotted vertical lines before the numbers (1–20) show the start of each fraction collected. The arrow marked feline pancreatic lipase (fPL) points to the only peak that shows lipolytic activity.
Figure 2:
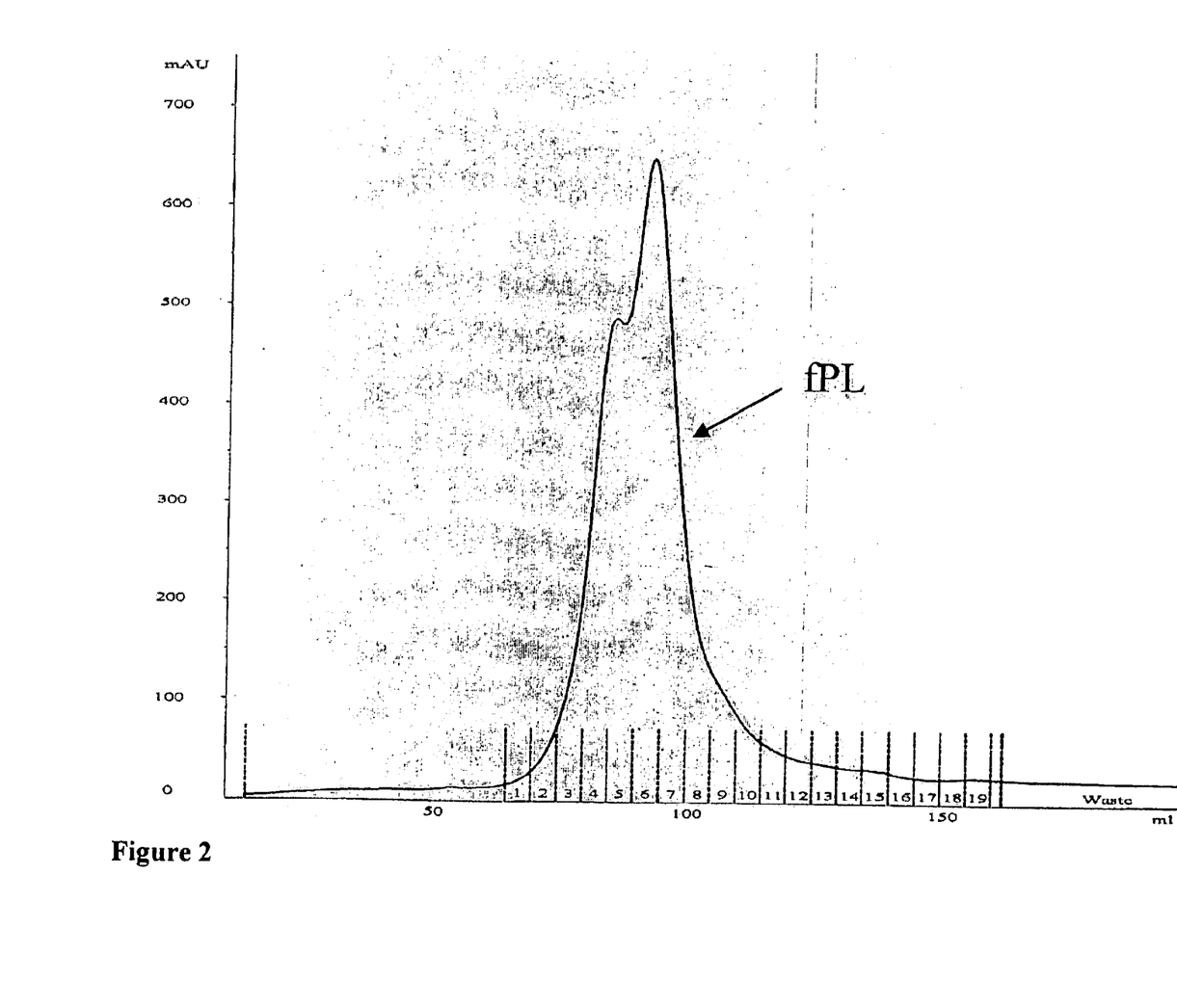
FIGS. 2 shows size-exclusion chromatography of partially purified feline pancreatic lipase (fPL). The curved line shows the absorbance at a wavelength of 280 nm during chromatography. The dotted vertical lines before the numbers (1–19) show the start of each fraction collected. The arrow points to the only peak with the lipolytic activity.
Figure 3:
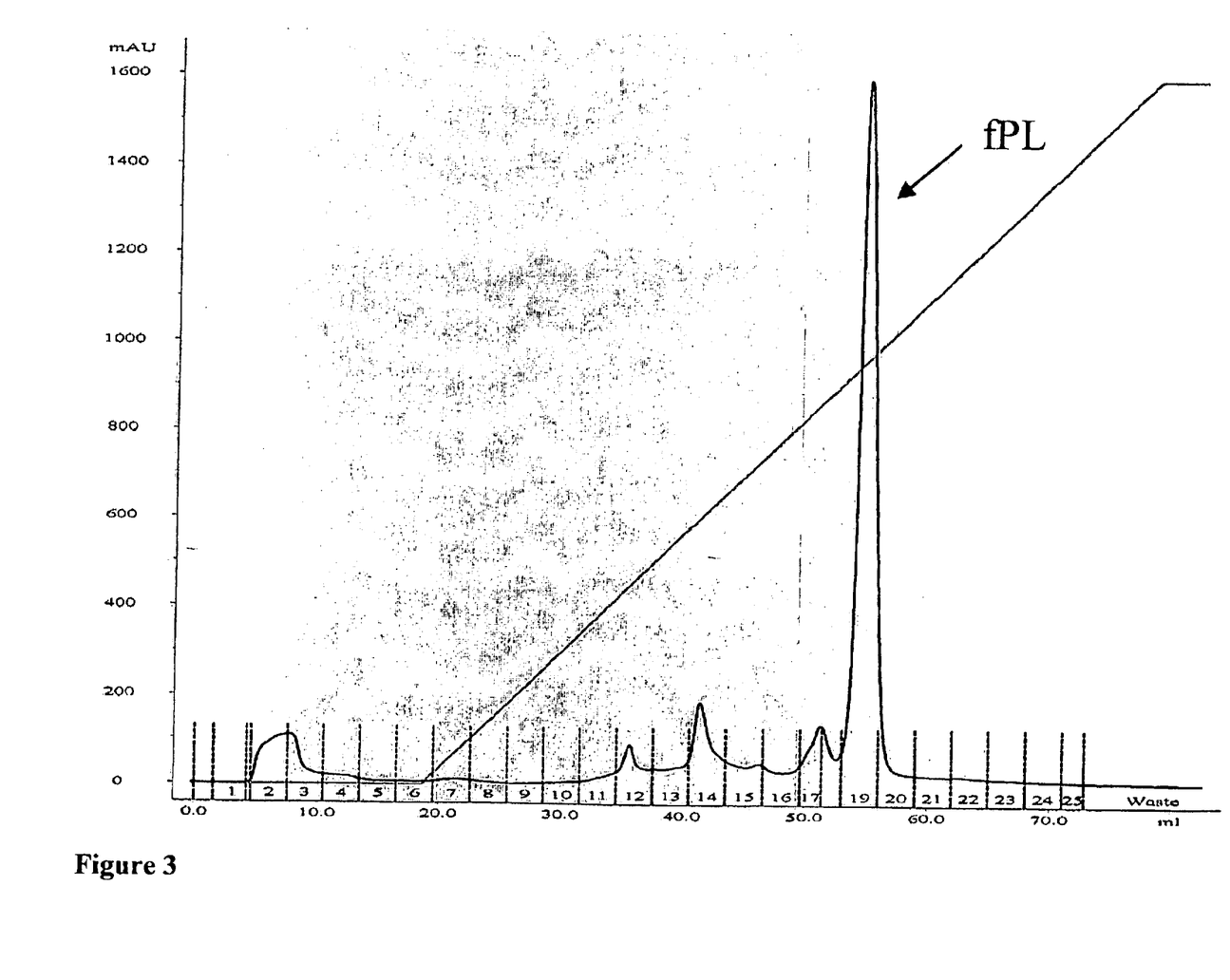
FIG. 3 shows cation-exchange chromatography of partially purified feline pancreatic lipase (fPL). The darker line shows the absorbance at a wavelength of 280 nm during chromatography. The lighter line shows the linear NaCl gradient ranging from 0 to 200 mM NaCl over 120 min. The dotted vertical lines before the numbers (1–25) show the start of each fraction collected. The arrow marks the only peak that shows lipolytic activity.
Figure 4:
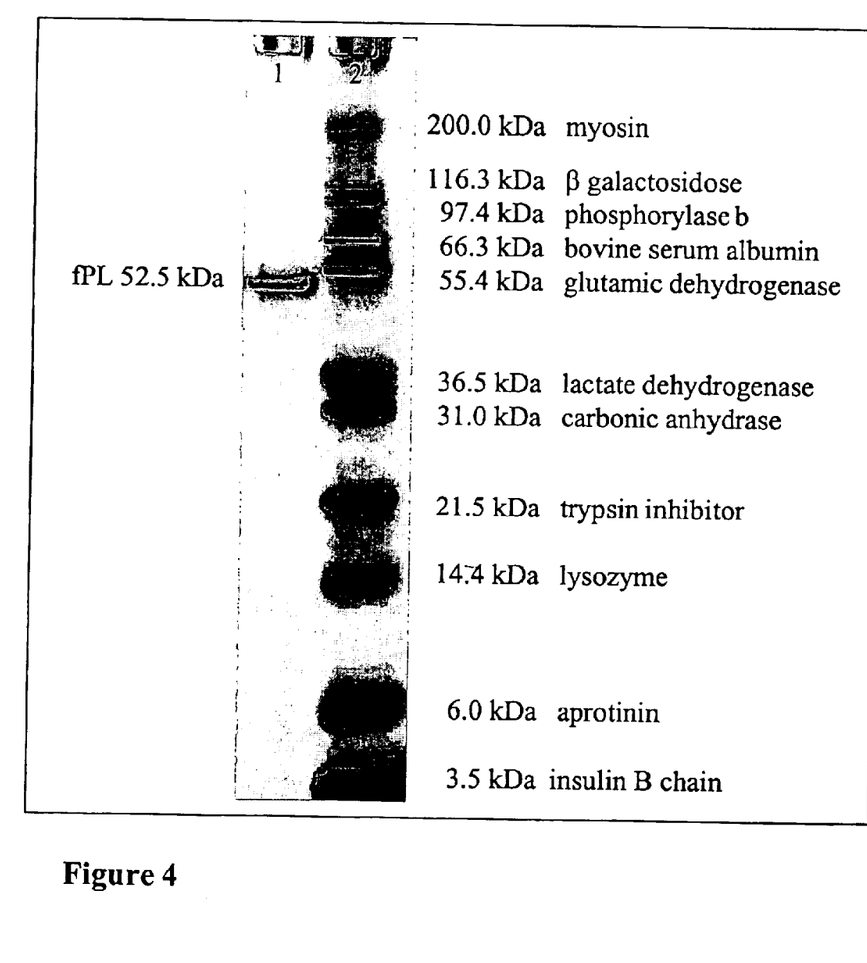
FIG. 4 shows SDS-PAGE result of feline classical pancreatic lipase. This SDS-PAGE gel was stained with a Coomassie blue stain. Purified feline classical pancreatic lipase (fPL) was loaded in lane 1, while a molecular weight standard (marker) was loaded in lane 2.

Feline pancreatic lipase was successfully purified from feline pancreatic tissue by delipidation of pancreatic tissue, protein extraction, anion-exchange chromatography (FIG. 1), size-exclusion chromatography (FIG. 2), and cation-exchange chromatography (FIG. 3; Table 1). Table 1 shows the sequential purification of feline classical pancreatic lipase from pancreatic tissue. The overall yield of the purification protocol was 18.6% (Table 1). The purified product showed a single band on sodium dodecyl sulfate polyacrylamide gel electrophoresis (SDS-PAGE) with a molecular mass of approximately 52.5 kDa (FIG. 4). Exact molecular mass was determined by mass spectrometry to be 52.4 kDa. Approximate specific absorbance at 280 m of fPL was 1.18 for a 1 mg/ml solution (Table 2). Table 2 shows the results for the estimation of the specific absorbance for fPL. A solution of fPL in PBS, pH 7.2 with an absorbance of $A_{280}=0.55$ was used as the starting solution and was analyzed in a BCA protein assay undiluted, in a 1 in 2 dilution, and in a 1 in 4 dilution.

TABLE 1

Purification of fPL

| Purification Stage | Volume (ml) | $A_{280}$ | Protein Content[1] (mg) | Specific Lipolytic Activity (U/mg) | Total Lipolytic Activity (U) | Yield (%) |
|---|---|---|---|---|---|---|
| aqueous pancreatic extract | 136.5 | 6.821 | 789.0 | 126 | 99,474 | 100.0 |
| post buffer exchange | 228.0 | 2.746 | 530.5 | 147 | 77,963 | 78.4 |
| post anion-exchange chromatography | 32.5 | 0.798 | 22.0 | 2,732 | 60,105 | 60.4 |
| post gel-filtration chromatography | 10.0 | 0.582 | 4.9 | 6,001 | 29,405 | 29.6 |
| post cation-exchange chromatography[2] | 3.85 | 0.550 | 1.8 | 10,261 | 18,470 | 18.6 |

[1]protein content was estimated using a specific absorbance of $A_{280} = 1.18$ for feline pancreatic lipase
[2]after concentration, buffer change, and adjustment of absorbance to $A_{280} = 0.550$

TABLE 2

Specific absorbance of fPL

| Dilution Factor | $A_{280}$ | Assay Result (µg/ml) | Adjusted Result (µg/ml) | Specific Absorbance |
|---|---|---|---|---|
| 1 | 0.550 | 472.86 | 472.86 | 1.163 |
| 2 | 0.275 | 227.67 | 455.34 | 1.208 |
| 4 | 0.1375 | 118.30 | 473.20 | 1.162 |
| Mean | | | | 1.178 |

Figure 5:
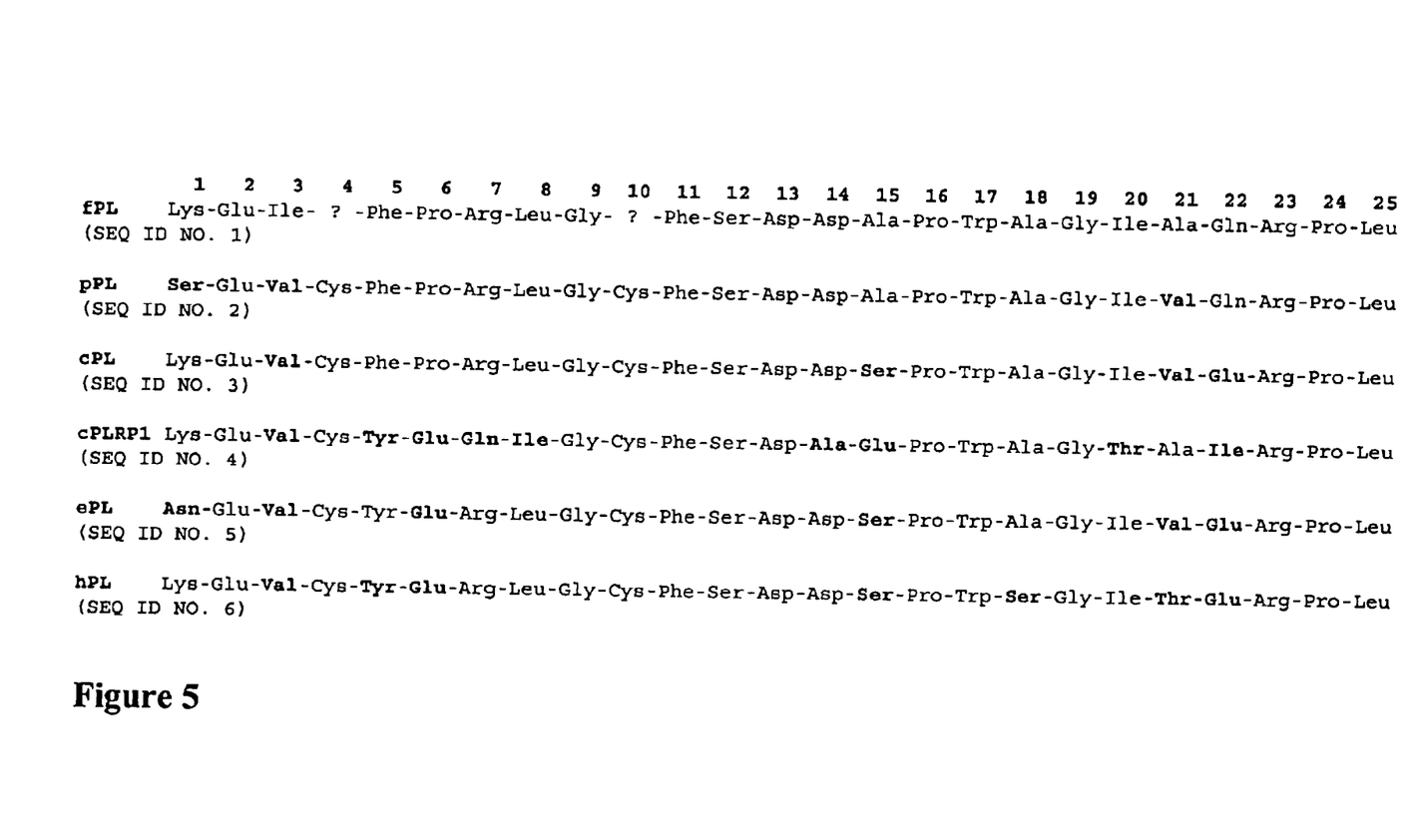
FIG. 5 shows N-terminal amino acid sequence of feline pancreatic lipase (fpL, SEQ ID NO. 1) in comparison with that of porcine pancreatic lipase (pPL, SEQ ID NO. 2), canine pancreatic lipase (cPL, SEQ ID NO. 3), canine pancreatic lipase related protein 1 (cPLRP 1, SEQ ID NO. 4), equine pancreatic lipase (ePL, SEQ ID NO. 5), and human pancreatic lipase (hpL, SEQ ID NO. 6). The amino acid sequences for ePL and hPL were deduced from cDNA sequence analysis. Amino acid residues that could not be identified are depicted by "?". Amino acid residues that are non-homologous with feline pancreatic lipase are shown in bold.

N-terminal amino acid sequence of the first 25 amino acid residues showed the sequence Lys-Glu-Ile-?-Phe-Pro-Arg-Leu-Gly-?-Phe-Ser-Asp-Asp-Ala-Pro-Trp-Ala-Gly-Ile-Ala-Gln-Arg-Pro-Leu (FIG. 5; ?=unknown). As shown in FIG. 5, this sequence has close homology with the N-terminal amino acid sequence of classical pancreatic lipase in other species.

EXAMPLE 5
Development and Validation of a Radioimmunoassay for the Measurement of Feline Pancreatic Lipase Immunoreactivity (FPLI) in Serum Serum lipase activity has classically been utilized for diagnosis of disorders of the exocrine pancreas in human beings and dogs. However, it is accepted that serum lipase activity is not specific for exocrine pancreatic function, and that many cell types other than pancreatic acinar cells synthesize lipases. Recently an assay for the measurement of canine pancreatic lipase immunoreactivity (cPLI) has been developed and validated. This assay has been shown to be specific for exocrine pancreatic function and sensitive for the diagnosis of pancreatitis in dogs. The present study developed and validated a radioimmunoassay for feline pancreatic lipase immunoreactivity (fPLI).

Pancreatic lipase was purified from feline pancreatic tissue by delipidation, anion-exchange chromatography, size-exclusion chromatography, and cation-exchange chromatography as described in above Example 1. Antiserum against feline pancreatic lipase (fPL) was raised in rabbits. Tracer was produced by iodination ($^{125}$I) of feline pancreatic lipase using the chloramine T method. A radioimmunoassay was established and validated by determination of sensitivity, dilutional parallelism, spiking recovery, intra-assay variability, and inter-assay variability. A control range for fPLI in cat serum was established from 30 clinically healthy cats using the central $95^{th}$ percentile.

The sensitivity of the fPLI assay was 1.2 µg/L. The observed to expected ratios for serial dilutions ranged from 58.0 to 164.3% for 4 different serum samples at dilutions of 1 in 2, 1 in 4, and 1 in 8. Observed to expected ratios for spiking recovery ranged from 76.0 to 156.5% for 4 different serum samples and 6 different spiking concentrations. Coefficients of variation for intra-assay variability for 4 different serum samples were 10.1, 4.5, 2.2, and 3.9%. Coefficients of variation for inter-assay variability for 4 different serum samples were 24.4, 15.8, 16.6, and 21.3%. The reference range (control range) was established as 2.0 to 6.7 µg/L.

This radioimmunoassay is sufficiently sensitive, linear, accurate, precise, and reproducible for clinical use. Such assays are readily adaptable to microtiter well-type and SNAPS devices (see e.g., U.S. Pat. No. 6,007,999; U.S. Pat. No. 5,750,333; U.S. Pat. No. 5,726,013; and U.S. Pat. No. 5,726,010; and the like).

EXAMPLE 6
Discussion

The present study provides the first detailed report of the purification of feline pancreatic lipase. Classical pancreatic lipase, a member of the pancreatic lipase gene family, has been identified in several vertebrate species (Vandermeers and Chroistophe, 1968; Rathelot et al., 1981; Bosc-Bierne et al., 1984; Gieseg et al., 1992; Mejdoub et al., 1994; Steiner and Williams, 2003). In many instances pancreatic lipase has been purified from pancreatic juice. This method was initially developed because aqueous extractions of pancreatic tissue led to the formation of a macromolecular form of pancreatic lipase, so-called fast lipase. Fast lipase is a macromolecular aggregate of pancreatic lipase, colipase, and lipids (Leger and Charles, 1980). However, the collection of pancreatic juice requires cannulation of the pancreatic duct and raises animal use concerns, especially when a non-invasive alternative such as the purification from pancreatic tissue collected from cats sacrificed for unrelated research projects is available. Delipidation procedures, using organic solvents, allow purification of pancreatic lipase from pancreatic tissue without the formation of fast lipase.

Reports of the specific absorbance of pancreatic lipase in any species could not be found. A BCA-based protein assay was used to estimate protein content in a solution of pure feline pancreatic lipase with a known absorbance at a wavelength of 280 nm (Smith et al., 1985). Bovine serum albumin was used as a standard in this assay. However, different proteins may have a different relative response in the BCA assay and determination of specific absorbance of feline pancreatic lipase by use of this assay may therefore be inaccurate (Smith et al., 1985). The estimated specific absorbance of feline pancreatic lipase can serve as a reproducible reference point for use of feline pancreatic lipase during further studies.

The purified material showed a single band on SDS-PAGE when stained with a Coomassie blue stain. The molecular mass of feline pancreatic lipase determined by mass spectrometry of 52.4 kDa compares to 50.7 kDa reported for canine pancreatic lipase, 52 kDa reported for porcine pancreatic lipase, 48 kDa for human and chicken pancreatic lipase, and 45 kDa for dromedary pancreatic lipase (De Caro et al., 1981; Bosc-Bierne et al., 1984; Bousset-Risso et al., 1985; Mejdoub et al., 1994; Steiner and Williams, 2003).

A total of 23 amino acid residues of the first 25 amino acid residues of the N-terminal amino acid sequence were identified. A comparison of the sequence for these 23 amino acids of feline classical pancreatic lipase showed a sequence homology of 87% with porcine classical pancreatic lipase, 83% with canine classical pancreatic lipase, 61% with canine pancreatic lipase related protein 1, 74% with equine classical pancreatic lipase, and 70% with human classical pancreatic lipase (FIG. 5) (Bianchetta et al., 1979; Winkler et al., 1990; Kerfelec et al., 1992; De Caro et al., 1998; Steiner and Williams, 2003). Two amino acid residues could not be determined, i.e., the residues in positions 4 and 10. Cysteine has been identified as the amino acid residue for both of these two positions in pigs, dogs, horses, and human beings. Given that cysteines can form disulfide bridges to form cystine that make them difficult to be identified it is hypothesized that amino acid residues in positions 4 and 10 of fPL are also cysteine. However, this hypothesis remains to be proven by repeated amino acid sequencing after reducing the sample.

Any patents or publications mentioned in this specification are indicative of the levels of those skilled in the art to which the invention pertains. Although the invention has been described with reference to specific embodiments, it is not thus limited but is susceptible to various changes and modifications without departing from the spirit thereof.

What is claimed is:

1. A method for measuring feline pancreatic lipase immunoreactivity in serum, comprising the steps of:
    preparing a serum sample from cats;
    preparing antiserum against feline pancreatic lipase;
    mixing the antiserum with the serum sample to form a mixture: and
    detecting a signal in the mixture, wherein the strength of the signal corresponds with the concentration of pancreatic lipase immunoreactivity, thereby measuring feline pancreatic lipase immunoreactivity in cat serum.

2. The method of claim 1, wherein feline pancreatic lipase has a N-terminal amino acid sequence comprising SEQ ID NO. 1.

3. The method of claim 1, wherein feline pancreatic lipase is labeled for evaluation of the antiserum during preparation.

4. The method of claim 3, wherein feline pancreatic lipase is radioiodinated ($^{125}$I).

5. The method of claim 4, wherein the signal is a radioactive signal.

6. The method of claim 1, wherein an elevation of the concentration of feline pancreatic lipase immunoreactivity above a control range corresponds with pancreatitis in cats.

7. The method of claim 6, wherein the control range for feline pancreatic lipase immunoreactivity in cat serum is established from a pool of healthy cats using the central $95^{th}$ percentile.

8. The method of claim 7, wherein the control range is from about 2.0 µg/L to about 6.7 µg/L.

* * * * *

SEQUENCE LISTING

```
<160> NUMBER OF SEQ ID NOS: 6

<210> SEQ ID NO 1
<211> LENGTH: 25
<212> TYPE: PRT
<213> ORGANISM: Felis catus
<220> FEATURE:
<221> NAME/KEY: Domain
<222> LOCATION: 4,10
<223> OTHER INFORMATION: N-terminal amino acid sequence of feline
      classical pancreatic lipase (fPL); Xaa - unknown

<400> SEQUENCE: 1

Lys Glu Ile Xaa Phe Pro Arg Leu Gly Xaa Phe Ser Asp Asp Ala
                 5                  10                  15

Pro Trp Ala Gly Ile Ala Gln Arg Pro Leu
                20                  25

<210> SEQ ID NO 2
<211> LENGTH: 25
<212> TYPE: PRT
<213> ORGANISM: Porcinus
<220> FEATURE:
<221> NAME/KEY: Domain
<222> LOCATION: 1...25
<223> OTHER INFORMATION: N-terminal amino acid sequence of porcine
      pancreatic lipase (pPL)

<400> SEQUENCE: 2

Ser Glu Val Cys Phe Pro Arg Leu Gly Cys Phe Ser Asp Asp Ala
                 5                  10                  15

Pro Trp Ala Gly Ile Val Gln Arg Pro Leu
                20                  25
```

```
<210> SEQ ID NO 3
<211> LENGTH: 25
<212> TYPE: PRT
<213> ORGANISM: Caninus
<220> FEATURE:
<221> NAME/KEY: Domain
<222> LOCATION: 1...25
<223> OTHER INFORMATION: N-terminal amino acid sequence of canine
      pancreatic lipase (cPL)

<400> SEQUENCE: 3

Lys Glu Val Cys Phe Pro Arg Leu Gly Cys Phe Ser Asp Asp Ser
                 5                  10                  15

Pro Trp Ala Gly Ile Val Glu Arg Pro Leu
             20                  25

<210> SEQ ID NO 4
<211> LENGTH: 25
<212> TYPE: PRT
<213> ORGANISM: Caninus
<220> FEATURE:
<221> NAME/KEY: Domain
<222> LOCATION: 1...25
<223> OTHER INFORMATION: N-terminal amino acid sequence of canine
      pancreatic lipase related protein      1(cPLRP 1)

<400> SEQUENCE: 4

Lys Glu Val Cys Tyr Glu Gln Ile Gly Cys Phe Ser Asp Ala Glu
                 5                  10                  15

Pro Trp Ala Gly Thr Ala Ile Arg Pro Leu
             20                  25

<210> SEQ ID NO 5
<211> LENGTH: 25
<212> TYPE: PRT
<213> ORGANISM: Equinus
<220> FEATURE:
<221> NAME/KEY: Domain
<222> LOCATION: 1...25
<223> OTHER INFORMATION: N-terminal amino acid sequence of equine
      pancreatic lipase (ePL)

<400> SEQUENCE: 5

Asn Glu Val Cys Tyr Glu Arg Leu Gly Cys Phe Ser Asp Asp Ser
                 5                  10                  15

Pro Trp Ala Gly Ile Val Glu Arg Pro Leu
             20                  25

<210> SEQ ID NO 6
<211> LENGTH: 25
<212> TYPE: PRT
<213> ORGANISM: Homo sapiens
<220> FEATURE:
<221> NAME/KEY: Domain
<222> LOCATION: 1...25
<223> OTHER INFORMATION: N-terminal amino acid sequence of human
      pancreatic lipase (hPL)

<400> SEQUENCE: 6

Lys Glu Val Cys Tyr Glu Arg Leu Gly Cys Phe Ser Asp Asp Ser
                 5                  10                  15

Pro Trp Ser Gly Ile Thr Glu Arg Pro Leu
             20                  25
```